United States Patent [19]

Boger

[11] 4,383,524
[45] May 17, 1983

[54] METHOD AND APPARATUS FOR AIDING IN CERVICAL SPINE RADIOGRAPHIC PRODUCTION

[76] Inventor: Donald C. Boger, 2727 E. Glenoaks, Glendale, Calif. 91206

[21] Appl. No.: 175,334

[22] Filed: Aug. 4, 1980

[51] Int. Cl.³ .............................................. A61H 1/02
[52] U.S. Cl. ................................... 128/75; 128/133; 128/DIG. 15
[58] Field of Search ............... 128/24 A, 31, 133, 134, 128/DIG. 15, 75, 653; 272/137, 142, 143

[56] References Cited

U.S. PATENT DOCUMENTS

| | | | |
|---|---|---|---|
| 798,367 | 8/1905 | Smokey | 128/31 |
| 905,301 | 12/1908 | English | 128/31 |
| 930,768 | 8/1909 | Kelly | 128/31 |
| 2,009,655 | 7/1935 | Freymann | 128/31 |
| 4,040,620 | 8/1977 | Friedman | 272/137 |
| 4,057,246 | 11/1977 | Wilson | 272/137 |
| 4,091,808 | 5/1978 | Nelson | 128/DIG. 15 |

Primary Examiner—John D. Yasko
Attorney, Agent, or Firm—Wagner & Bachand

[57] ABSTRACT

A traction aid for lowering the shoulders during lateral cervical spine radiographic procedures. The device employs a pair of wrist cuffs joined by an adjustable loop which extends around the underside of the feet of a supine patient. Straightening the knees and extending the feet tensions the patient's arms and depresses his shoulders allowing improved exposure of the sixth and seventh vertebrae to lateral X-ray procedures. In an alternate embodiment a pair of shoulder straps encircle the patient's shoulders and are joined by the leg straps to depress the shoulders by direct pressure on the shoulders. The mechanical interaction between the straps and the straightening of the legs and feet produces the required depression. The method of this invention involves the use of such a traction device and the patient's voluntary or the doctor's manual straightening of the legs with minimum exposure to the radiation field.

9 Claims, 11 Drawing Figures

METHOD AND APPARATUS FOR AIDING IN CERVICAL SPINE RADIOGRAPHIC PRODUCTION

BACKGROUND OF THE INVENTION

Frequently in hospital emergency rooms as well as in other clinical settings, neck injuries necessitate radiographs to be taken. Accurate lateral radiographs of this region of the body are difficult to obtain because of the interference from the shoulders. The radiographs of the cervical or neck region of the vertebral column are taken from a lateral view to disclose possible injury. The shoulders often naturally block the view of the part of the sixth and all of the seventh vertebrae on the radiograph allowing injury of these last two vertebrae to go undetected.

To obtain radiographs of this region of the body it is a common practice to have a doctor suppress the shoulders of the patient in an attempt to get a clear view of the cervical vertebrae. Disadvantages of this method are that caudal displacement of the shoulders by the doctor frequently is not adequate to clear the view of the entire cervical area, and the physician undesirably risks exposure to radiation.

Today, the only method to displace the shoulders of a patient needing neck radiographs is mentioned above along with its disadvantages. No mechanical aids have been developed specifically for this purpose. Devices for restraint during the taking of X-rays are illustrated by U.S. Pat. Nos. 3,358,141 and 3,933,154. Both of these devices utilize many straps and a back plate to totally immobilize the patient, usually babies or small children. Neither of these devices could cause the required manipulation of the shoulders to achieve the desired results.

Other devices which are for restraint purposes are U.S. Pat. Nos. 1,596,792; 3,247,843; and 3,776,540. None of these devices work with the desired part of the body to cause shoulder suppression.

Exercise devices which use straps over various parts of the body are seen in U.S. Pat. Nos. 1,663,641 and 3,655,185. Both patents require that there be active involvement by the person using the device. To attempt to use these on a person with neck injuries would be unsuccessful due to the fact that these people often come into the emergency room in an unconscious or weakened state.

None of the aforementioned devices illustrate the auto-traction of the arms by the straightening of the legs to depress the shoulders. By using a strap around the wrists which meets under the feet and straightening of the legs causes a tensioning of the strap which results in depression of the shoulders to a degree such that the neck region is clear of shoulder obstruction for radiography.

BRIEF DESCRIPTION OF THE INVENTION

Through many years of working with a hospital emergency department, I have come to realize the need for a quick, simple device and method to take accurate radiographs of all seven cervical vertebrae in the neck of a patient. Most patients with neck injuries can offer only a minimum of assistance in suppressing their shoulders for a clearer view of the cervical vertebrae during radiography.

It became clear to me that by mechanical assistance in pulling the arms downward toward the feet and allowing the head to be free from restraint, a natural displacement of the shoulders takes place within the body. This reaction by the body to the traction of the arms is such that more cervical vertebrae are exposed upon radiography. The degree of shoulder depression is greater than if one merely presses down on the shoulders, or if the doctor pulls the arms downward. Sufficient caudal displacement of the shoulders which exposes the entire cervical series of vertebrae is evident in radiographs and hardly visible by the external position of the body. This reinforces the fact that detection of injuries to the sixth and seventh cervical vertebrae is difficult.

I have developed a traction device consisting of two separate T-shaped straps. The head of the "T" attaches around the wrists and the leg of the "T" extends along side of the body of the strap from the other arm. The site of attachment of the two straps is under the soles of the feet by the hook and eye fastening material, known by the trademark "Velcro."

Additional applications of this device are recognized in therapeutic radiation of the face or neck. The traction device serves to remove the shoulders out of the field of unnecessary radiation without any discomfort to the patient resulting directly from the traction.

In an alternate embodiment, shoulder depression is achieved by shoulder straps encircling the shoulders and acting directly via the same straps which encircle the feet in the primary embodiment.

BRIEF DESCRIPTION OF THE DRAWINGS

The foregoing brief description of this invention may be more clearly understood from the following detailed description and the drawing in which.

DETAILED DESCRIPTION OF THE DRAWING

Figure 1:
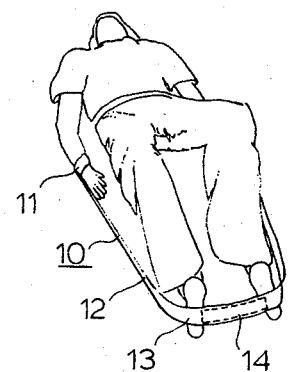
FIG. 1 is a perspective view of the traction device when applied to the patient just prior to use.
Figure 2:
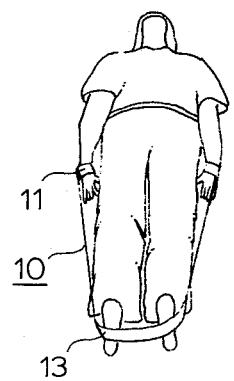
FIG. 2 is a perspective view of the traction device of FIG. 1 in traction.

As a result of my need for a method to depress a patient's shoulders in the taking of cervical radiographs, I have developed a device as seen in FIGS. 1 and 2. Refer now to FIG. 1 wherein the patient is in the supine position while wearing the traction device of this invention, generally designated 10 with cuff straps 11 around his wrists, and the body 12 of the device extending along the sides of the patient and under the soles of his feet. The end regions 13 of the straps meet under the soles of the feet and fasten with a continuously adjustable fastening means, such as Velcro. In FIG. 1 the patient's knees are bent, therefore, at this time there is no tension on the straps nor is there shoulder suppression.

FIG. 2 is an illustration of active use of the traction device by the patient's body. The knees are straightened thereby causing the tension in the straps 10a and 10b which draws the arms downward and depresses the shoulders.

Figure 3:
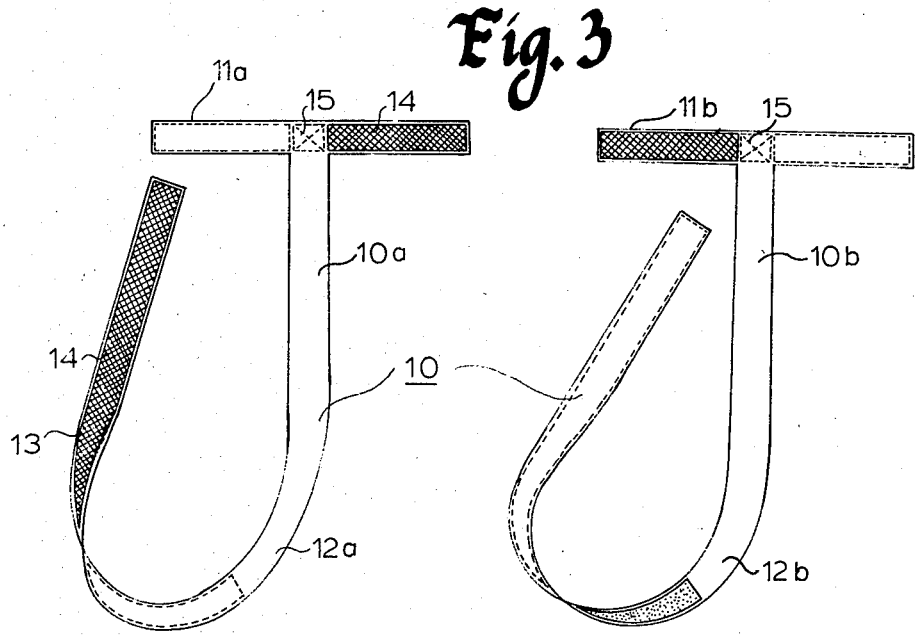
FIG. 3 is an elevational view of the basic traction device showing parts from which it is made.

FIG. 3 is a front view of the traction device 10 which is made up of two straps 10a and 10b which include short cuff straps 11a and 11b for wrist attachment, and longer body members 12a and 12b. Each body member 12a and 12b is attached perpendicular to its respective cuff strap 11a or b as by stitching. Both the cuff straps 11a and 11b and the end regions 13a and 13b are fastened by means of a continuously adjustable fastening means 14. Specifically, this continuously adjustable fastening means is located on the cuff straps 11a and 11b and the end regions 13 and made up by a hook and eye part such that when one brought into contact with the other, a union is made.

The preferred embodiment of the traction device 10 consists of an inextensible fabric tape for the entire device in which the head of the "T" or cuff straps 11 measures 14 inches long by 2 inches wide and the body portion 12 of the device is 50 inches long by 2 inches wide. The upper two inches of the body portion 12 overlaps the cuff strap 11 and are attached by stitching 15. On the cuff straps 11, opposing sides of Velcro tape 14 measuring 5.5 inches long by 1.5 inches wide are centered and attached. On each body portion 12, Velcro 14 measuring 28.5 inches long and 1.5 inches wide is centered and attached. This amount of adjustable fastening means 14 allows for the traction device to fit patients ranging from small children to adults.

Figure 4:
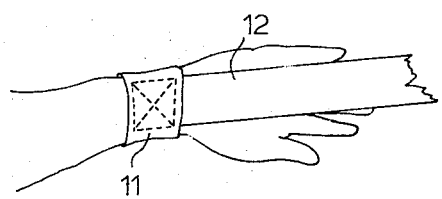
FIG. 4 is a fragmentary perspective view of the traction device showing the cuff strap as attached to a wrist.

FIG. 4 is an enlarged view of the cuff strap 11 fastened to a wrist showing the effective attachment of the body member 12. Present in the union of the cuff strap 11 and the body member 12 is stitching in a square pattern 15 with an "X" in the middle of the square which gives the union added strength.

Figure 5:
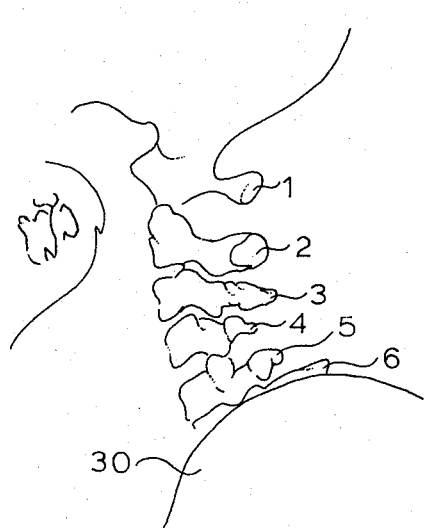
FIG. 5 is a reproduction of a lateral radiographic view of cervical vertebrae with depression of the shoulders by prior art methods.
Figure 6:
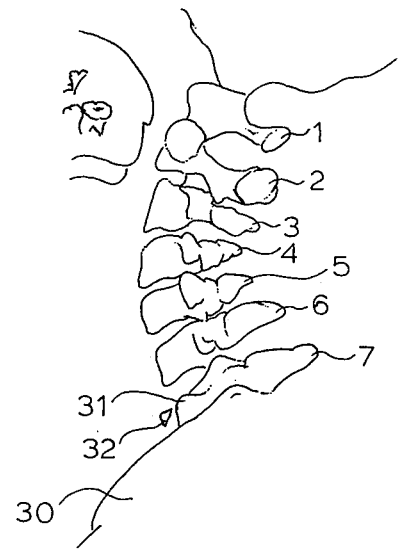
FIG. 6 is a reproduction of a lateral radiographic view of cervical vertebrae with depression of the shoulders using the traction device.

FIGS. 5 and 6 are both lateral views of the cervical vertebrae taken from actual radiographs. FIG. 5 is representative of the degree of shoulder 30 suppression by conventional manual means. In this drawing, as it was seen in the radiograph only the first five vertebrae are exposed in full and only a part of the sixth is visible.

FIG. 6 is showing the greater degree of shoulder displacement which takes place using the traction device of this invention. The shoulder is lowered such that the sixth and seventh vertebrae are more clearly visible. In this particular case, a chip 32 of the seventh vertebrae 31 was detected because of this method of exposing the cervical vertebrae after having been undetected using prior art techniques.

As seen in FIGS. 1, 2, 8, and 9, the method used in accordance with the invention to depress the shoulders of the patient prior and during cervical radiograph examination involves placing the patient in a horizontal position on his back with knees slightly elevated. The patient's wrists are secured to an inextensible strap which then extends along the side of the patient and under the feet of the patient. The patient's knees are depressed by the patient voluntarily or by downward pressure applied to the knees by the doctor or his assistant. The patient's feet press against the resistence of the inextensible strap using the knees as a mechanical two-bar linkage to caudally depress the shoulders for cervical radiograph.

Contraindication of the device is in cases of significant upper extremity, bilateral lower extremity, thoracic or lumbar spine trauma. Usage of this device is inappropriate in these situations, as the traction may aggravate the injuries. However, the device of FIGS. 7, 10 and 11 avoids contact with the upper extremities and may be used for patients with injuries to the upper extremities.

An optional feature of this device is a shoulder attachment which fastens to the traction device by means such as the hook and eye fabric fastener. The attachment is used in cases where arm injuries inhibit use of the traction device in its original form. Shoulder depression is achieved by a harness encircling the shoulder region of the body and attaching to the original tractional device which is then secured under the soles of the feet. In the event of actual or suspected shoulder injury this embodiment likewise should not be used.

In the case of arm injury the inextensible strap is secured around the shoulders and attached under the feet in the same manner as described above.

Figure 7:
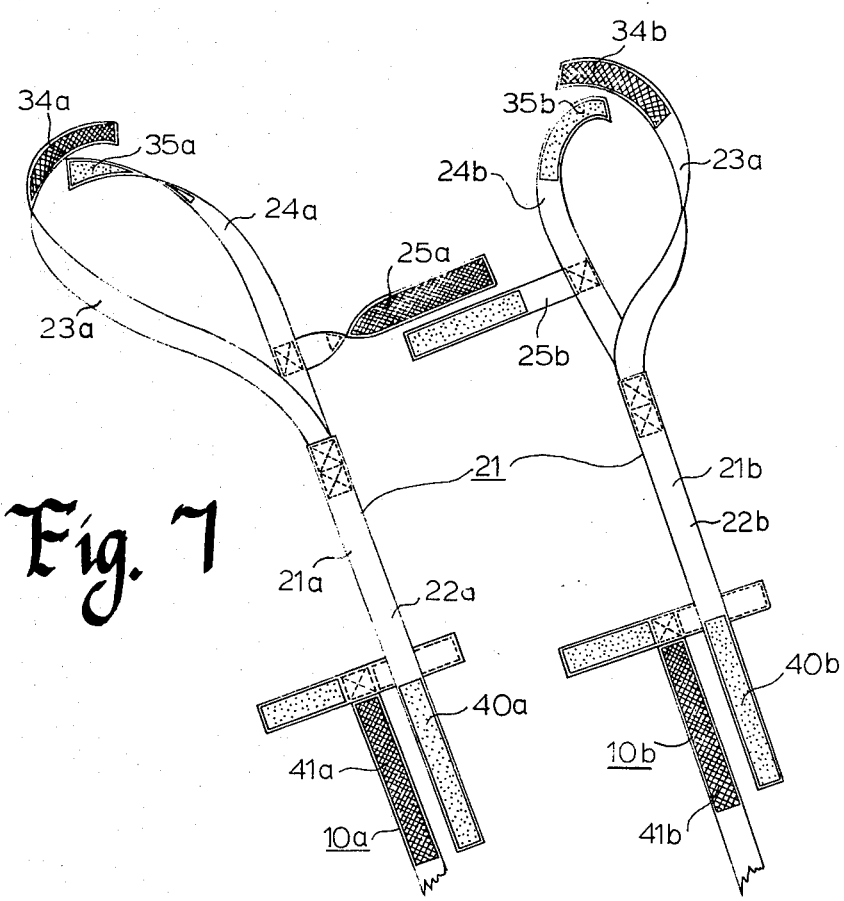
FIG. 7 is a perspective view of a shoulder attachment illustrating its relationship with the traction device of FIGS. 1 through 4.

Now referring to FIG. 7 a shoulder attachment 21a and b made up of four straps for each shoulder; a base strap 22a and 22b, two shoulder straps 23a and b and 24a and b, and a back strap 25a and b. The two shoulder straps 23 and 24 are attached to the upper end of the base strap 22 and form a shoulder loop where the opposing sides of the hook and eye fasteners 34a and b and 35a and b meet. The back strap 25a is sewn to the rear shoulder strap 24a and fastens to the other back strap 25b on the opposing half of the shoulder attachment 21b. Usage of the attachment 21 is recommended when a patient has actual or suspected injury to the upper extremities. To achieve shoulder depression in these situations, the shoulder attachment 21 is attached to the traction device 10 at the body 12 by additional hook and eye fastener 40a and 40b, joining matching fastener means 41a and 41b.

Figure 10:
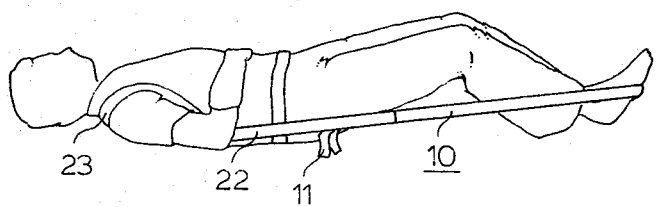
FIG. 10 is a side view of the alternate traction embodiment applied around the shoulder of a patient just prior to traction.
Figure 11:
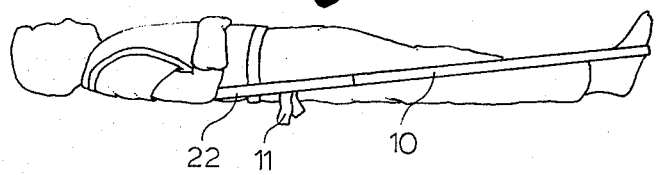
FIG. 11 is a side view in accordance with FIG. 10 during traction.
Figure 8:
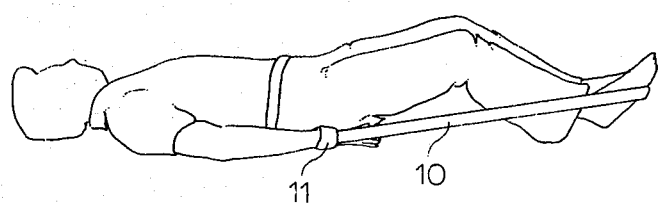
FIG. 8 is a side view of the traction device applied to a patient just prior to use.
Figure 9:
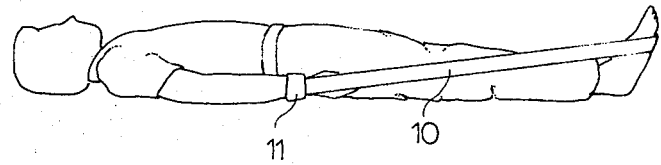
FIG. 9 is a side view in accordance with FIG. 8 during traction.

This modified version of my invention extends around the patient's shoulders and under the soles of his feet. The end regions 13 of the original traction device 10 provide the straps which extend under the feet as illustrated in FIG. 10. The wrist straps are unused. Shoulder depression is achieved again when the knees are straightened and the toes extended against the resistance of the straps when the body is in the supine position. This position is illustrated in FIG. 11. In the case of arm injury as seen in FIGS. 10 and 11 the shoulder straps 21 are attached while the right arm is in a cast and rests unhampered on the patient's chest.

The foregoing constitute techniques of the best made known by me of carrying out this invention. The scope of this invention is not limited to the specific embodiment shown but rather to the invention as defined by the following claims including equivalents therefor.

What is claimed is:

1. A body tensioning device for depressing the human shoulder to facilitate the taking of radiographs of the cervical region of a patient comprising elongated strap means including end regions and adjustable length intermediate region;

said end regions comprise a pair of strap portions for each shoulder of adjustable length dimensioned to encircle the shoulders of a patient and join the said intermediate region in the underarm area along the sides of the patient;

said end regions and intermediate region being adjustable in length to depress the patient's shoulders upon the extension of the patient's feet.

2. The combination in accordance with claim 1 wherein said legs of the T of each strap contains continuously adjustable fastening means.

3. The combination in accordance with claim 1 wherein said end regions and said intermediate region are adjustable by means of hook and eye fabric contained on mating surfaces thereof to provide a controllable adjustment of the size of the wrist opening therein and the overall length of said body tensioning device.

4. The combination in accordance with claim 1 wherein the body of said member is fabricated from relatively inextensible fabric tape material.

5. The combination in accordance with claim 1 including cross strap means extending between a strap for each shoulder.

6. The combination in accordance with claim 1 wherein said regions are all continuously adjustable.

7. The method of depressing the shoulders of the patient prior and during cervical radiograph examination comprising the steps of:
placing the patient in a horizontal position on his back with the knees elevated and heels generally at the level of the buttocks;
securing the wrists of the patient to a relatively inextensible flexible member having overall length less than the distance around the feet of the patient when lying flat and the wrists unrestrained;
placing the relatively inextensible flexible device around the underside of the patient's feet; and
depressing the patient's knees toward the plane of the buttocks whereby the patient's arms and shoulders are drawn downward by the reaction of the extension of his feet.

8. The method in accordance with claim 7 wherein the depression of the patient's knees is by the exertion of the patient's own energy.

9. The method in accordance with claim 7 wherein the knees of the patient are depressed manually by another third person standing adjacent to the patient prior to exposure to radiography.

* * * * *